United States Patent [19]

O'Brien et al.

[11] Patent Number: 4,681,612
[45] Date of Patent: Jul. 21, 1987

[54] PROCESS FOR THE SEPARATION OF LANDFILL GAS

[75] Inventors: John V. O'Brien, Shrewsbury, Mass.; Arthur S. Holmes, LaCrosse, Wis.; Richard B. Hopewell, Medfield, Mass.

[73] Assignee: Koch Process Systems, Inc., Westboro, Mass.

[21] Appl. No.: 822,311

[22] Filed: Jan. 24, 1986

Related U.S. Application Data

[63] Continuation-in-part of Ser. No. 615,577, May 31, 1984, abandoned.

[51] Int. Cl.4 .................................................. F25J 3/06
[52] U.S. Cl. ............................................ 62/23; 55/16; 55/23; 55/57; 55/68; 62/40
[58] Field of Search ............... 62/11, 17, 23–31, 62/40; 55/16, 23, 25, 57, 58, 68, 76

[56] References Cited

U.S. PATENT DOCUMENTS

| | | | |
|---|---|---|---|
| 2,888,807 | 6/1959 | Bocquet | 62/11 |
| 4,000,990 | 1/1977 | Bingham | 55/30 |
| 4,130,403 | 12/1978 | Cooley et al. | 55/16 |
| 4,152,129 | 5/1979 | Trentham et al. | 62/18 |
| 4,157,247 | 6/1979 | Collins, III et al. | 55/31 |
| 4,529,411 | 7/1985 | Goddin, Jr. et al. | 62/24 |

FOREIGN PATENT DOCUMENTS

| | | | |
|---|---|---|---|
| 1017637 | 1/1966 | European Pat. Off. | 55/16 |
| 110858 | 4/1984 | United Kingdom | 55/16 |

Primary Examiner—Ronald C. Capossela
Attorney, Agent, or Firm—Richard P. Crowley

[57] ABSTRACT

A recycle process for the separation of landfill gas containing a wide variety of impurities into a carbon dioxide product stream and a fuel-grade-pressurized methane product stream, the process providing for the removal of both the impurities and the carbon dioxide in a cryogenic column as a bottom stream, the separation of the methane from the overhead product stream by a membrane process, and, optionally, the removal of impurities from the carbon dioxide bottom stream in a separate purification column, to recover a high-quality, liquid, carbon dioxide stream.

31 Claims, 1 Drawing Figure

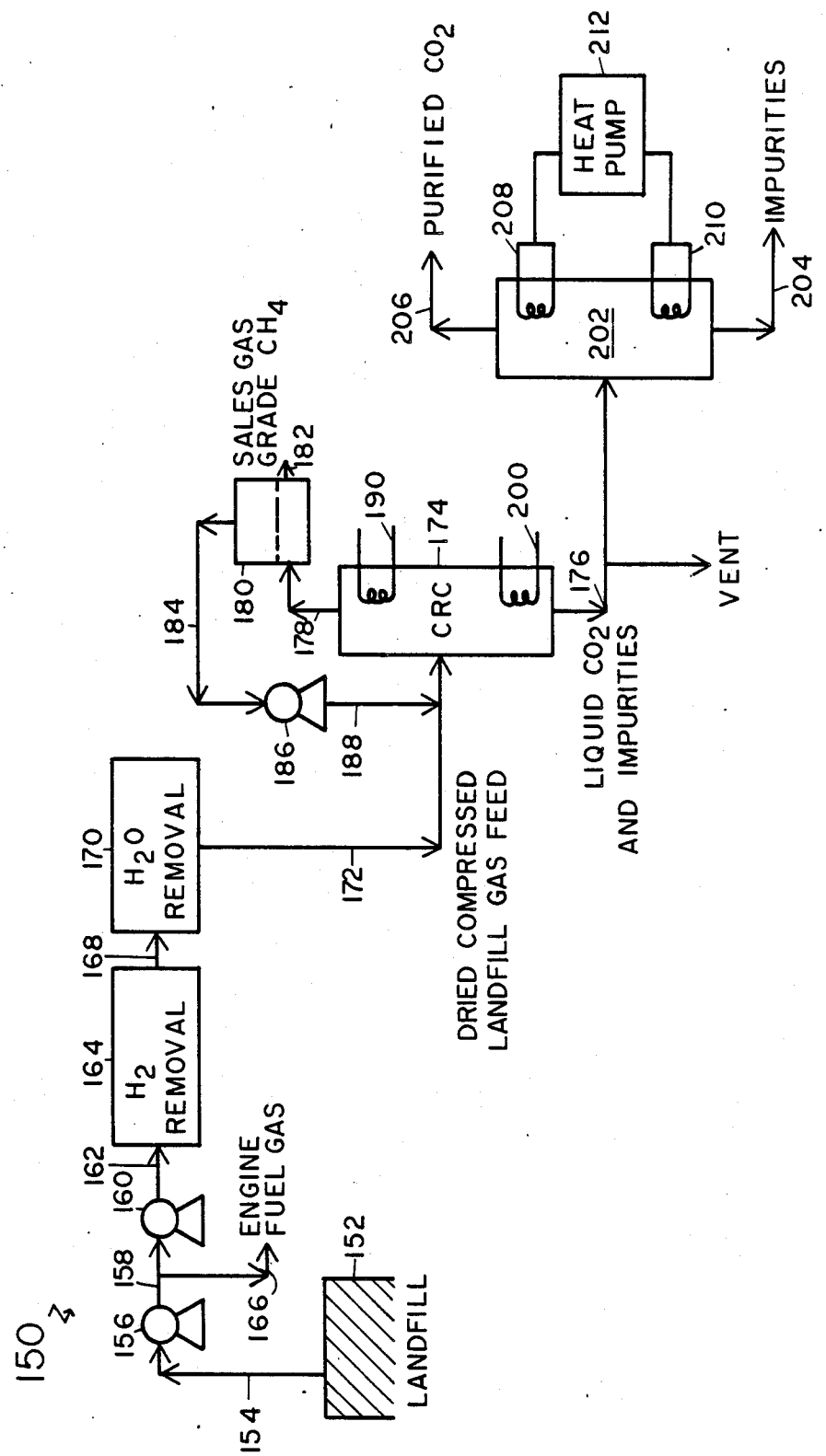

PROCESS FOR THE SEPARATION OF LANDFILL GAS

REFERENCE TO PRIOR APPLICATION

This application is a continuation-in-part of U.S. Ser. No. 615,577, filed May 31, 1984 now abandoned.

BACKGROUND OF THE INVENTION

Typically, landfill gas or biogas derived from a landfill comprises generally equally molal amounts of a mixture of carbon dioxide and methane, with the carbon dioxide and methane representing about 90 mole percent or more of the biogas. The landfill gas also contains minor amounts of nitrogen, oxygen, hydrogen, carbon monoxide and a variety of undesirable trade impurities present at the ppm level, as well as water vapor. The nitrogen and oxygen content of the biogas depends on the air ingress to the landfill- and gas-collection system. Generally, the landfill gas is extracted by employing a slight vacuum on a pipework manifold which is buried in the landfill. Landfill gas so extracted is then typically compressed and burned as a source of heat. Occasionally, such low BTU gas is used to fuel a generator for the direct production of electric power.

It is desirable to provide from the landfill gas methane of fuel-grade or sales-gas quality, typically with no more than 3 mole percent, or, more preferably, no more than 2 mole percent carbon dioxide content. Such high-grade fuel is readily marketable and widely useful. It is desirable also to obtain a high-purity carbon dioxide stream typically in liquid form, for sale at a purity of up to food-grade quality; that is, containing generally less than 10 parts per million of methane. A lower product quality may be acceptable, if the carbon dioxide liquid is to be employed as a refrigerating fluid or for well-field injection or other purposes. In these cases, a carbon dioxide product, containing up to 5 mole percent methane or other trace impurities, is typically usable.

The separation of the landfill gas into a liquid carbon dioxide product stream and a compressed fuel-quality methane product stream in an efficient and economical manner presents several problems. Landfill gas streams may be separated employing cryogenic fractionation in a cryogenic distillation column; however, in such cryogenic fractionation, while it can achieve a food-grade liquid carbon-dioxide product stream, the resulting methane stream contains at least 15 mole percent of carbon dioxide and is unsatisfactory for use as a sales-quality or fuel-grade gas stream without significant further processing.

The landfill gas stream also may be cryogenically fractionated employing the Ryan/Holmes process as described in U.S. Pat. No. 4,318,423, issued Mar. 9, 1982. In the Ryan/Holmes process, a first distillation column is employed to produce a methane stream as an overhead product, while carbon dioxide, plus ethane and heavier hydrocarbons, are produced as a bottom product stream. Since the carbon dioxide would normally freeze at the temperature encountered in a demethanizer, the Ryan/Holmes process employs a liquid additive agent, such as an alkane (like a $C_3$–$C_6$) stream fed into the column which effectively prevents the freeze up of carbon dioxide in the column, so as to prevent acid gas solids, such as carbon dioxide, from occurring in the solids-potential zone of the column. However, the Ryan/Holmes process requires the introduction of an additive agent, and further results in the contamination of the bottom product stream containing the carbon dioxide with the additive agent, and, therefore, further processing steps are required, in order to recover carbon dioxide and to remove the additive agent.

The landfill gas stream may be treated in a multiple-stage gas-permeation membrane-type process or alternatively in a pressure-swing-adsorption process, to provide for the separation of the methane and carbon dioxide; however, such processes cannot achieve a high-purity liquid carbon dioxide product stream, while further the carbon dioxide product stream obtained is a vapor at a low pressure and would require significant further processing, to obtain a high-quality liquid carbon dioxide product stream.

The impurities or contaminants in a landfill gas may vary in type and amount, but typically contaminant moisture is generally at a saturated level, while nitrogen ranges from 0.5 to 4 percent; oxygen 0 to 1 percent; hydrocarbons (nonmethane) from about 500 to 4,000 ppm; halocarbons, oxygenated and sulfonated hydrocarbons from about 100 to 2,000 ppm; hydrogen sulfide from about 2 to 100 ppm; and carbon monoxide up to about 1,000 ppm. Various separate techniques and steps are employed to remove these trace contaminants from the landfill biogas; for example, but not limited to: for moisture, the use of refrigeration dryers, pressure-swing dryers, thermal-swing dryers and glycol scrubbers; for nitrogen, fractional distillation; and for oxygen, fractional distillation and deoxo units. For nonmethane hydrocarbons, activated carbon adsorption and catalytic oxidation are used, and for halocarbons, oxygenated and sulfonated hydrocarbons, activated carbon adsorption and catalytic oxidation are used. In the case of hydrogen sulfide, iron-sponge adsorption, impregnated-charcoal adsorption, and molecular-sieve adsorption techniques are used, and for carbon monoxide, generally catalytic oxidation.

Gas-permeation membrane apparatuses have been used in combination with a distillation column for the separation of an azeotropic mixture of carbon dioxide and ethane (see, for example, U.S. Pat. No. 4,374,657, issued Feb. 23, 1983). However, this process is directed to the particular process problems associated with carbon dioxide/ethane azeotropic feed streams, and does not provide for use of a landfill biogas or provide a high-purity carbon dioxide stream and a fuel-grade methane stream.

It is, therefore, desirable to provide a simple, effective and economical process for the separation of landfill biogas containing impurities into a high-quality carbon-dioxide vapor or liquid product stream and a fuel-grade compressed methane product stream.

SUMMARY OF THE INVENTION

The invention relates to the separation of a landfill feed stream, high in both methane and carbon dioxide and containing impurities, into a methane product stream and into a high-content carbon dioxide product stream. In particular, the process concerns the treatment and separation of a landfill or biogas feed stream in a simple recycle process into a high-purity liquid carbon dioxide product stream and into a compressed fuel-grade methane product stream, while rejecting the wide variety of impurities present in the landfill gas stream.

The process of the invention is directed to the treatment and separation of a landfill biogas feed stream containing impurities in a recycle process into a carbon dioxide and methane product stream. The process comprises: extracting the biogas gas feed stream from the landfill; compressing the gas feed stream; optionally removing hydrogen from the compressed gas feed stream; drying the gas feed stream; and then separating the resulting dry, pure, pressurized gas feed stream into the desired product streams.

The separation process is carried out by separating the compressed landfill gas stream through the use of a combination of a methane purifier and a cryogenic distillation column. A methane purifier comprising a gas membrane-permeation apparatus is designed to produce a highly purified fuel-grade methane product stream, while the cryogenic or low-temperature distillation column produces a liquid carbon dioxide bottom product stream containing most of the impurities. The overhead product stream from the distillation column is recycled through the methane membrane purifier system, thereby providing for a recycle-type process which is simple, economical and effective in recovering commercially valuable product streams.

The cryogenic column unexpectedly captures essentially most of the impurities and contaminants in the bottom stream with the carbon dioxide. Optionally, these impurities and contaminants may be removed in a carbon dioxide purification column (CPC), where high-quality carbon dioxide is recovered as an overhead product stream, and the impurities and contaminants removed with a bottom product stream.

Also, where a high-purity methane stream is not required, the overhead methane-enriched stream from the cryogenic column need not be sent to a methane purifier, but may be withdrawn for other use or process treatment as required, and no recycle to the cryogenic column of the overhead product stream need be made. In this embodiment, the high-content carbon dioxide/methane feed gas stream from the landfill is introduced into the cryogenic column, a methane-enriched overhead stream is withdrawn, a carbon-dioxide-enriched bottom stream is withdrawn, which stream contains substantially all of the landfill-gas impurities, the bottom product stream is introduced as a feed stream into a carbon dioxide purification apparatus, such as a low-temperature purification distillation column, and a purified carbon dioxide overhead product stream is withdrawn for use, and a bottom product stream, containing essentially all of the landfill-gas impurities, is withdrawn for further processing, treatment or disposal. For example, the methane-enriched overhead stream, free of landfill impurities, may contain about 15% to 35% carbon dioxide and be used for fuel or other purposes, or the carbon dioxide could be removed, if desired, by other than a membrane process.

The process is applicable to the separation of landfill gas which contains a wide variety of undesirable impurities, in addition to the desirable methane and carbon dioxide. It has been discovered that an unexpectedly high number and amount of these undesirable impurities are removed with the bottom product stream containing the carbon dioxide in a cryogenic fractionation column, to separate the methane and carbon dioxide. The process eliminates the necessity for a plurality of separate process steps, such as the use of adsorption beds, such as activated charcoal beds, to remove these undesirable impurities before the separation of the carbon dioxide and methane.

The process comprises: introducing a compressed, dry, landfill gas feed stream, containing substantial amounts of carbon dioxide and methane, together with very minor amounts of undesirable impurities and contaminants, into a cryogenic carbon dioxide recovery column (CRC); withdrawing a liquid bottom product stream enriched in carbon dioxide and containing a high amount or essentially most of the undesirable impurities; and withdrawing a methane-enriched overhead product stream. The process includes introducing the methane-enriched overhead product stream into a methane purifier, particularly a gas-permeable membrane apparatus; withdrawing from the methane purifier a compressed sales-grade, purified methane product stream; withdrawing from the methane purifier a carbon dioxide-enriched membrane permeate stream; compressing the carbon dioxide permeate stream; and recycling the compressed permeate carbon-dioxide-enriched stream into the cryogenic distillation column or the landfill gas feed stream for the column.

The process provides an overhead methane-enriched product stream from the cryogenic column which often is of or approaches sales-product quality. The high degree of removal of the impurities with the bottom product stream is surprising and unanticipated and provides significant process advantages. The removal of the impurities in the liquid bottom stream avoids the necessity of alternative removal techniques, such as the use of activated charcoal beds, typically a batch-type process, where the charcoal beds are not regenerable, leading to high capital costs and additional processing. In contrast, the process provides for a continuous distillative process, where the recovered impurities in the bottom product stream can be disposed of by venting or separate processing. Optionally, where a high-quality carbon dioxide product stream is to be recovered, the process includes introducing the carbon dioxide-enriched bottom product stream, containing the impurities as a feed stream, into a carbon dioxide purification column (CPC); withdrawing a high-quality, essentially impurities-free carbon dioxide overhead product stream; and withdrawing a bottom product stream containing all or essentially all the impurities for disposal or further processing. The use of a purifier distillation column, to produce a high-quality carbon dioxide product stream, also eliminates the need for extensive adsorption beds or other processes, to remove the recovered impurities. If desired, any residual $C_3+$ impurities in the carbon dioxide stream may be removed, to provide a food-grade carbon dioxide product.

Thus, in the process a dry, compressed feed stream is first introduced into a distillation column for the recovery of a liquid purified carbon dioxide stream as a bottom product stream from said column, while the overhead product stream rich in methane is directed into a methane purifier system, and a purified, compressed, high-methane-content product stream is recovered from the methane purifier system, while a high carbon dioxide stream from the methane purifier system is then recycled, compressed and reintroduced into the distillation column.

The process provides for the production of a carbon dioxide product stream in varying degrees of purity, such as and more particularly a high purity stream commonly termed a liquid carbon dioxide product stream characterized in having less than about 10 parts per million of methane or a lower quality liquid carbon dioxide stream; for example, having less than 5 mole percent of methane, or a vapor carbon dioxide product stream under pressure, or a vapor carbon dioxide product stream which may be vented to atmosphere, where a liquid carbon dioxide stream is not produced. The liquid carbon dioxide product stream may be employed, for example, in low-temperature distillative-column refrigeration, such as by vaporizing and recycling the carbon dioxide product stream, which may reduce or eliminate the need for any external refrigeration systems.

The process of the invention avoids the need to introduce a liquid additive agent or a solvent into the low-temperature distillation column or the subsequent separations required, where such additive agents or solvents are so employed. The process is a simple, economical and efficient recycling process which is particularly adapted for use of landfill biogas or for other feed streams, wherein there is a high amount of methane and carbon dioxide in the original feed streams. Typically, such feed streams would represent over about 90 mole percent, or more typically 92 to 95 mole percent or greater, of generally equal amounts of methane and carbon dioxide in the feed stream with lesser amounts of impurities, such as nitrogen and oxygen, and minor amounts of hydrogen, carbon monoxide, hydrocarbons, oxygenated hydrocarbons like ketones, halogenated hydrocarbons, together with water vapor present in the original landfill feed stream.

The feed stream of the process generally is derived from a landfill; however, the biogas feed stream may be obtained from other sources, provided only that there are high amounts, generally of about equal volumes, of methane and carbon dioxide in the feed stream, for example, and usually representing from about 30 to 70; for example, 40 to 60, mole percent of the feed stream, and the feed stream contains undesirable impurities and contaminants as in or similar to a landfill gas. In the past, landfill biogas has been used principally for the heating value of the gas and for providing electricity or has been purified for fuel use only. The conventional approach is marginally economically attractive and usually produces methane only. The present invention provides for a combination of steps in a simple recycle process, to provide for two commercially usable product streams, thereby substantially improving the economics of the system.

The gas produced by a landfill is typically extracted under a slight vacuum. The landfill gas generally is contaminated with atmospheric oxygen and nitrogen and also contains water vapor, which should be removed or reduced prior to introduction into the carbon dioxide recovery column. The landfill gas may also contain low or trace quantities of sulfur compounds and halogenated hydrocarbons. These impurities must be removed, when a food-grade, high-purity liquid carbon dioxide stream is to be produced. Initially the landfill gas is boosted in pressure by a gas-extraction blower to between about 5 and 50 psig.

In the past, trace contaminant removal was accomplished by a variety of techniques, such as, for example, but not limited to, the employment of adsorption or absorption beds containing activated charcoal or molecular-sieve material, to adsorb or absorb the trace contaminants. Generally, landfill gas is extracted by the gas-extraction blower, trace contaminants are then removed, and the trace-contaminant-free landfill gas is then compressed and cooled; for example, by a gas compressor, to a pressure generally greater than about 250 psig; for example, 350 to 900 psig, and at temperatures ranging from about 70° F. to 150° F. The fuel gas for the gas compressor can be taken from the landfill feed stream.

The pressurized, dried, landfill gas feed stream is introduced to the methane/carbon dioxide separation process, which comprises a methane purification apparatus and a cryogenic distillation column. The overhead stream from the distillation column is recycled to the methane purifier stage, and the increased carbon dioxide content stream from the methane purifier stage is recycled to the carbon dioxide distillation column. The methane purification apparatus is designed to produce two streams: a high-purity methane product stream, typically of sales-gas quality and containing less than about 2 mole percent of carbon dioxide; and a stream which is rich in carbon dioxide; that is, with increased carbon dioxide content over the feed stream introduced into the methane purification apparatus.

The methane purification apparatus, where employed, may comprise any process or apparatus to remove carbon dioxide from the compressed methane-enriched overhead stream, such as a gas-membrane apparatus, as well as adsorption beds or chemical and physical processes, such as the use of solvents or reactants like the Selexol process, to remove carbon dioxide and to permit the removed carbon dioxide to be recycled back to the cryogenic methane/carbon dioxide separation column. The methane purification apparatus may comprise a gas-permeable membrane whose gas-separation factors lead it to result in a pure methane stream with a reasonable methane recovery. For example, the gas-permeation membrane may comprise one or more single or multiple-series stages of a gas-permeation membrane module containing a cellulose acetate, such as a cellulose-triacetate-purported gas-permeation membrane, such as disclosed in U.S. Pat. No. 4,130,403, typically either in hollow-fiber or spiral-membrane module form. The resulting high-purity, fuel-grade methane product stream is retained at the compressed pressure suitable for use, while the resulting carbon dioxide-rich permeate stream is at a reduced pressure.

A liquid carbon dioxide bottom product stream is produced by the employment of a cryogenic distillation column, typically operated at a pressure of about 200 to 900 psia at a temperature typically above about $-70°$ F., to produce a liquid carbon dioxide product stream as a bottoms product stream containing the impurities. The overhead product stream removed from the cryogenic column generally contains from about 10 to 40 mole percent carbon dioxide; for example, 15 to 30 mole percent.

The carbon-dioxide-enriched permeate stream from the methane purifier apparatus typically is at a low pressure, generally atmospheric pressure to about 100 psig, and is enriched in the carbon dioxide, in comparison to the column overhead feed stream. This carbon-dioxide-rich permeate stream is then compressed, generally to about 200 to 900 psig, and then introduced back into the cryogenic distillation column. The column contains a plurality of standard separation stages, trays or packing, together with a reboiler and a condenser designed to produce a liquid carbon dioxide product stream as a bottom product stream, and a column overhead product stream containing carbon dioxide and methane, which is recycled to the methane purification apparatus.

In the process, the landfill feed stream is introduced first directly into a cryogenic distillation column and the column overhead product stream is then introduced into the methane purification apparatus. In this arrangement, where the feed stream is introduced first into the cryogenic column, the flow to the membrane purification apparatus, such as the gas-permeation membrane system, is much reduced, as is the recycle flow from the methane purification apparatus to the column. The permeate from the methane purification, such as from a gas-permeation membrane, is compressed generally to the cryogenic column operating pressure, and the permeate product stream then may be blended directly with the feed stream to the cryogenic column or fed to an appropriate location directly into the distillation column.

The carbon dioxide purification apparatus may comprise any apparatus or process for the recovery of a purified carbon dioxide from the carbon-dioxide-enriched bottom product stream and the separation of the impurities from the purified carbon-dioxide stream. Generally, such purification is easily carried out employing a low-temperature distillation column containing fractionation trays, with the pressure and temperature of the column selected to follow the equilibrium pressure and temperature for the recovery of the purified carbon dioxide. In the use of such purifier column, it has been found that the temperature gradient in the separation of the carbon dioxide and the landfill-gas impurities is quite low; for example, about 2° F. or less, so that the purification process lends itself to the use of a heat pump with associated low-energy consumption in the operation of the purification column.

Where treatment of the impurities is required to remove contaminants and/or impurities, such as by adsorption or catalytic oxidation, the process is advantageous, since the flow containing the contaminants is much reduced from the flow of the original landfill feed stream, due to the concentration of the contaminants either in the bottom product stream with the carbon dioxide or in the bottom product stream from the $CO_2$ purification column.

The invention is described for the purposes of illustration only; however, it is recognized that various changes, modifications and improvements to the process as illustrated and described may be made by those persons skilled in the art, all of which changes, modifications and improvements fall within the spirit and scope of the invention.

BRIEF DESCRIPTION OF THE DRAWING

The drawing represents a general schematic process-flow diagram of the process and includes the optional use of a carbon dioxide purification column in the process.

DESCRIPTION OF THE EMBODIMENTS

The drawing shows a schematic general process-flow scheme 150 employing a landfill 152, wherein a landfill-gas feed stream containing impurities is extracted through line 154 by an extraction blower 156, sent through line 158 to a gas compressor 160 and a compressed feed gas withdrawn through line 162 and directed to a hydrogen-gas removal process in a deoxo or catalytic hydrogen removal process 164, and the hydrogen-free feed gas removed via line 168 and dried in a dehydrator 170 for the removal of saturated water vapor to a dew point of generally less than −70° F. Optionally as illustrated, a fraction of the feed gas may be removed via line 166 to be employed as an engine fuel gas to run the gas compressors. A hydrogen-free dehydrated feed stream is removed from the dehydrator 170 via line 172 and introduced into a low-temperature cryogenic distillation column 174; that is, a carbon dioxide recovery column (CRC), adapted for the separation of methane and carbon dioxide, and a liquid carbon dioxide product stream removed as a bottom product stream via line 176, together with essentially all of the impurities. The CRC includes a condenser 190 and a reboiler 200. The bottom product stream may be vented to atmosphere as illustrated, or optionally the carbon dioxide recovered as purified carbon dioxide.

An overhead column product stream rich in methane is removed via line 178 and introduced into a methane purifier, such as a gas-permeation membrane apparatus 180, and a sales-gas-grade methane product stream is removed by line 182, while a low-pressure carbon-dioxide-enriched permeate product stream is removed via line 184, recompressed in compressor 186 and introduced via line 188 into the feed stream 172 going to the distillation column 174, or optionally, as desired, introduced into a desired portion of the column, as illustrated by the dotted line from line 188. In the process-flow scheme illustrated, the feed stream introduced into the column is high in carbon dioxide and, therefore, the distillation column 174 is upstream of the methane purification apparatus 180. An alternative configuration for this scheme is to locate a dehydration system after the extraction blower 156 and combine the compression duties for 160 and 186 in one compression.

Where a purified liquid carbon dioxide stream is desired, the liquid carbon dioxide bottom product stream, with the impurities from CRC 174, is removed via line 176 and is introduced as a feed stream into a low-temperature cryogenic distillation column 202; that is, a carbon dioxide purification column (CPC), said column containing a reboiler 210 and a condenser 208 which is particularly suited to operate with a heat pump 212. A purified carbon dioxide overhead product stream is withdrawn via line 206, while the landfill-gas impurities, comprising hydrocarbons like $C_3$–$C_4$ sulfur compounds, oxygenated hydrocarbons, halogenated hydrocarbons and the like, are withdrawn as a bottom product stream via line 204.

Computer-derived simulations were employed to simulate process conditions within the distillation and purifier columns of the drawing. The computer program employed is known as the PROCESS simulation program from Simulation Sciences Inc., Fullerton, Calif., while the vapor liquid equilibrium data for the methane/carbon dioxide system was calculated, based on the Peng Robinson equation of state. Tables I and II provide data for a simulated composition of a typical landfill biogas stream and the process conditions at various stages in the process-flow diagram of the drawing.

TABLE I

| STREAM NO. & DESCRIPTION | 154 BIOGAS FEED STREAM PPM | 172 BIOGAS STREAM FROM DEHYDRATOR PPM | 184 MEMBRANE PERMEATE STREAM PPM | 178 CRC OVERHEAD STREAM PPM | 182 $CH_4$ SALES GAS STREAM PPM | 176 LIQUID $CO_2$ AND IMPURITIES STREAM PPM | 206 PURIFIED LIQUID $CO_2$ STREAM PPM | 204 IMPURITIES STREAM PPM |
|---|---|---|---|---|---|---|---|---|
| Paraffins: | | | | | | | | |
| Propane | 750.0 | 751.1 | 546.5 | 293.7 | — | 1613.5 | 1522.2 | 1978.1 |
| Butane | 20.0 | 20.0 | 1.5 | 0.8 | — | 43.0 | 5.9 | 191.2 |
| Pentane | 15.0 | 15.0 | — | — | — | 32.3 | 0.1 | 160.7 |
| Hexane | 15.0 | 15.0 | — | — | — | 32.3 | — | 161.1 |
| Sub-total | 800.0 | 801.1 | 548.0 | 294.5 | — | 1721.1 | 1528.2 | 2491.1 |
| Aromatics: | | | | | | | | |
| Benzene | 2.0 | 2.0 | — | — | — | 4.3 | — | 21.5 |
| Toluene | 40.0 | 40.0 | — | — | — | 86.1 | — | 429.7 |
| Ethylbenzene | 5.0 | 5.0 | — | — | — | 10.8 | — | 53.7 |
| Xylenes (as para) | 15.0 | 15.0 | — | — | — | 32.3 | — | 161.1 |
| Sub-total | 62.0 | 62.0 | — | — | — | 133.5 | — | 666.0 |
| Ethers: | | | | | | | | |
| Tetrahydrofuran | 5.0 | 5.0 | — | — | — | 10.8 | — | 53.7 |
| Sub-total | 5.0 | 5.0 | — | — | — | 10.8 | — | 53.7 |
| Ketones: | | | | | | | | |
| Acetone | 15.0 | 15.0 | — | — | — | 32.3 | — | 161.1 |
| Methyl Ethyl Ketone | 20.0 | 20.0 | — | — | — | 43.0 | — | 214.9 |
| Methyl Isobutyl Ketone | 1.0 | 1.0 | — | — | — | 2.1 | — | 10.7 |
| Sub-total | 36.0 | 36.0 | — | — | — | 77.4 | — | 386.7 |
| Halogens: | | | | | | | | |
| Chloromethane | 1.0 | 1.0 | 0.1 | — | — | 2.1 | 0.3 | 9.5 |
| Vinyl Chloride | 10.0 | 10.0 | 0.5 | 0.3 | — | 21.5 | 1.7 | 100.6 |
| Chloroethane | 2.0 | 2.0 | — | — | — | 4.3 | — | 21.3 |
| Methylene Chloride | 25.0 | 25.0 | — | — | — | 53.8 | — | 268.6 |
| 1,1 Dichloroethene | 1.0 | 1.0 | — | — | — | 2.1 | — | 10.7 |
| Trans-1,2-Dichloroethene | 5.0 | 5.0 | — | — | — | 10.8 | — | 53.7 |
| 1,1-Dichloroethane | 5.0 | 5.0 | — | — | — | 10.8 | — | 53.7 |
| 1,2-Dichloropropane | 1.0 | 1.0 | — | — | — | 2.1 | — | 10.7 |
| Trichloroethene | 5.0 | 5.0 | — | — | — | 10.8 | — | 53.7 |
| 1,1,1,-Trichloroethane | 1.0 | 1.0 | — | — | — | 2.1 | — | 10.7 |
| Tetrachloroethene | 5.0 | 5.0 | — | — | — | 10.8 | — | 53.7 |
| Trichloroflouromethane | 1.0 | 1.0 | — | — | — | 2.1 | — | 10.7 |
| Dichlorodiflouromethane | 35.0 | 35.0 | 3.4 | 4.9 | 6.6 | 67.7 | 29.8 | 219.2 |
| Sub-total | 97.0 | 97.0 | 4.0 | 5.2 | 6.6 | 201.0 | 31.8 | 876.8 |
| TOTAL | 1000.0 | 1001.1 | 552.0 | 299.7 | 6.6 | 2143.8 | 1560.0 | 4474.3 |

TABLE II

| STREAM NO. & DESCRIPTION COMPONENT | 154 BIOGAS FEED STREAM | | 172 BIOGAS STREAM FROM DEHYDRATOR | | 184 MEMBRANE PERMEATE STREAM | | 178 CRC OVERHEAD STREAM | |
|---|---|---|---|---|---|---|---|---|
| | Mol./Hr. | Mol. % | Mol./Hr. | Mol. % | Mol./Hr. | Mol. % | Mol./Hr. | Mol. % |
| $CO_2$ | 520.45 | 47.40 | 520.45 | 47.47 | 339.26 | 49.84 | 350.98 | 27.71 |
| $CH_4$ | 524.84 | 47.80 | 524.84 | 47.87 | 312.22 | 45.86 | 836.56 | 66.04 |
| $N_2$ | 40.63 | 3.70 | 40.63 | 3.71 | 23.48 | 3.45 | 64.11 | 5.06 |
| CO | 1.10 | 0.10 | 1.10 | 0.10 | 063 | 0.09 | 1.73 | 0.14 |
| $H_2$ | 1.10 | 0.10 | — | — | — | — | — | — |
| $O_2$ | 8.78 | 0.80 | 8.23 | 0.75 | 4.76 | 0.70 | 12.99 | 1.02 |
| IMPURITIES | 1.10 | 0.10 | 1.10 | 0.10 | 0.38 | 0.06 | 0.38 | 003 |
| TOTAL | 1098.00 | 100.00 | 1096.35 | 100.00 | 680.73 | 100.00 | 1266.75 | 100.00 |
| MMSCFD (GPM) | 10.000 | | 9.985 | | 6.200 | | 11.537 | |
| TEMP. °F. | 80 | | 100 | | 80 | | −45 | |
| PRESS. PSIA | 15 | | 665 | | 45 | | 650 | |

| STREAM NO. & DESCRIPTION COMPONENT | 182 $C_4$ SALES GAS STREAM | | 176 LIQUID $CO_2$ AND IMPURITIES STREAM | | 206 PURIFIED LIQUID $CO_2$ STREAM | | 204 IMPURITIES STREAM | |
|---|---|---|---|---|---|---|---|---|
| | Mol./Hr. | Mol. % | Mol./Hr. | Mol. % | Mol./Hr. | Mol. % | Mol./Hr. | Mol. % |
| $CO_2$ | 11.72 | 2.00 | 508.73 | 99.67 | 406.99 | 99.72 | 101.74 | 99.55 |
| $CH_4$ | 524.34 | 89.48 | 0.50 | 0.10 | 0.50 | 0.12 | — | — |
| $N_2$ | 40.63 | 6.93 | — | — | — | — | — | — |
| CO | 1.10 | 0.19 | — | — | — | — | — | — |
| $H_2$ | — | — | — | — | — | — | — | — |
| $O_2$ | 8.23 | 1.40 | — | — | — | — | — | — |
| IMPURITIES | <0.01 | 6.6 ppm | 1.10 | 0.21 | 0.64 | 0.16 | 0.46 | 045 |
| TOTAL | 586.02 | 100.00 | 510.33 | 100.00 | 408.13 | 100.00 | 102.20 | 100.00 |
| MMSCFD (GPM) | 5.337 | | (54.4) | | (43.5) | | (10.9) | |
| TEMP. °F. | 80 | | 51 | | −45 | | −42 | |

TABLE II-continued

| PRESS. PSIA | 630 | 660 | 133 | 138 |
|---|---|---|---|---|

The above tables show the landfill feed gas stream composition with the impurities therein and the stream compositions and process conditions at various stages of the process illustrated in the drawing. Surprisingly, the results show that a major portion, and for some constituents essentially all, of the undesirable trace contaminants and impurities in a typical landfill-gas stream are removed with a liquid bottom stream from the CRC. The overhead methane product stream from the CRC is virtually pure enough with respect to the trace impurities for direct use as a sales- or fuel-grade methane stream. The overhead stream is further enhanced and enriched in methane by passage through the gas-permeation membrane which removes; that is, prevents the passage of, the carbon dioxide.

The CRC bottom product stream is easily separated by distillation or other means; for example, the carbon dioxide purification column (CPC), to produce a high-purity carbon dioxide stream essentially free of the landfill-gas impurities. In the CPC, over 80 mole percent of the feed stream is recovered as a purified carbon dioxide product stream. The data show that all the impurities are fractionated out of the carbon dioxide feed stream by the purification column, except for some propane, butane, pentane, chloromethane, vinyl chloride and dichlorodifluoromethane (Freon 11). The purified carbon dioxide overhead stream contains the following impurities:

|  | ppm |
|---|---|
| Propane | 1522.2 |
| Butane | 5.9 |
| Pentane | 0.1 |
| Chloromethane | 0.3 |
| Vinyl chloride | 1.7 |
| Dichlorodifluoromethane | 29.8 |

Thus, as shown, of the listed trace impurities, the removal percentages are:

| Paraffins: | |
|---|---|
| Propane | 24+% |
| Butane | 89+% |
| Pentane and heavier | 99+% |
| Aromatics: | 100% |
| Ethers: | 100% |
| Ketones: | 100% |
| Halogens: | 87+% |

Other undesirable impurities that will be removed by the process, but which were not simulated, are as follows:

| S Compounds | HC Similar | Approx. % Removal |
|---|---|---|
| MeSH | $nC_4$–$iC_5$ | 80–90 |
| EtSH and heavier mercaptans | $nC_5$+ | 99+ |
| $Me_2S$ | $nC_5$ | 99+ |
| $CS_2$ | $nC_5$ | 99+ |

The purification column is illustrated as operating at pressures below 200 psi and at a low temperature; for example, less than −40° F. As shown by the data, the temperature gradient in the purification distillation is less than 5° F.; for example, 3° F., so the illustrated purification fractionation process is well suited to the use of a heat pump, to reduce the energy composition.

The process of the invention as demonstrated is an efficient, economical recycle process for the separation of landfill-type gas streams, to produce two valuable product streams.

What is claimed is:

1. A recycle process for the separation of a landfill feed gas stream, having a high concentration of methane and carbon dioxide and containing undesirable trace gas impurities, into a fuel-or sales-grade gas methane product stream and a liquid carbon dioxide product stream, which process comprises:
   (a) introducing an essentially hydrogen-free, dried, compressed, landfill feed gas stream into a cryogenic distillation column;
   (b) withdrawing a methane-enriched overhead product stream from said distillation column;
   (c) withdrawing an enriched liquid carbon dioxide bottom product stream, containing a major amount of the undesirable impurities, from said distillation column;
   (d) introducing the methane-enriched overhead product stream into a gas-permeation membrane apparatus;
   (e) withdrawing from said membrane apparatus a sales- or fuel-grade gas methane product stream;
   (f) withdrawing from said membrane apparatus a carbon-dioxide-enriched gas permeate stream;
   (g) compressing the carbon-dioxide-enriched gas permeate stream; and
   (h) recycling the compressed permeate stream for use in the process.

2. The process of claim 1 wherein the feed gas stream has a concentration of carbon dioxide and methane of over about 90 mole percent of the feed gas stream.

3. The process of claim 1 wherein the feed gas stream has a concentration of both carbon dioxide and methane of over about 90 mole percent, and the carbon dioxide and methane are present in generally about equal concentrations.

4. The process of claim 1 wherein the feed gas stream comprises from about 30 to 70 mole percent of carbon dioxide and 30 to 70 mole percent of methane.

5. The process of claim 1 wherein the methane product stream consists essentially of methane having less than about 3 mole percent of carbon dioxide.

6. The process of claim 1 wherein the liquid carbon dioxide product stream from said distillation column consists essentially of liquid carbon dioxide having less than about 5 mole percent of methane and essentially all undesirable impurities.

7. The process of claim 1 which comprises treating with landfill feed gas stream, to dry the feed gas stream to a dew point generally of −70° F. or lower.

8. The process of claim 1 which comprises compressing the carbon-dioxide-enriched stream from the gas-permeation membrane apparatus and introducing the compressed carbon-dioxide-enriched stream into said distillation column at a temperature of about 0° F. or below.

9. The process of claim 1 wherein the methane-enriched overhead product stream from said distillation column comprises about 10 to 40 mole percent of carbon dioxide.

10. The process of claim 1 wherein the carbon-dioxide-enriched stream withdrawn from the methane purification apparatus comprises more than about 50 mole percent of carbon dioxide.

11. The process of claim 1 which includes venting the carbon-dioxide-enriched bottom product stream containing the impurities.

12. The process of claim 1 which includes processing the liquid carbon-dioxide-enriched bottom product stream, to remove the impurities, and recovering a purified liquid carbon dioxide product stream.

13. The process of claim 1 wherein the undesirable impurities comprise sulfur compounds, halogenated hydrocarbon compounds, ketones and hydrocarbons.

14. The process of claim 1 which includes:
    (a) introducing the liquid carbon-dioxide-enriched bottom product stream as a feed stream into a low-temperature purification distillation column;
    (b) withdrawing a purified carbon dioxide overhead product stream from said purification column; and
    (c) withdrawing a bottom product stream containing essentially all of the undesirable impurities.

15. The process of claim 14 wherein the purified carbon dioxide overhead product stream consists essentially of a purified carbon dioxide product stream.

16. The process of claim 14 which includes treating the bottom product stream containing essentially all of the undesirable impurities, to remove such impurities.

17. The process of claim 16 which includes employing a heat pump in the operation of the purification column.

18. The process of claim 14 which includes operating the said purification distillation column under pressure and temperature conditions, to provide a temperature difference of less than about 5° F. in the said column.

19. The process of claim 1 wherein the recycled, compressed permeate stream is introduced into the landfill gas feed stream.

20. The process of claim 1 wherein the recycled, compressed permeate stream is introduced directly into said distillation column.

21. A recycle process for the apparatus of a landfill feed gas stream, having a high concentration of methane and carbon dioxide and containing undesirable trace gas impurities, into a fuel- or sales-grade gas methane product stream and a liquid carbon dioxide product stream, which process comprises:
    (a) introducing an essentially hydrogen-free, dried, compressed, landfill feed gas stream into a cryogenic distillation column;
    (b) withdrawing a methane-enriched overhead product stream from said distillation column;
    (c) withdrawing an enriched liquid carbon dioxide bottom product stream, containing a major amount of the undesirable impurities, from said distillation column;
    (d) introducing the methane-enriched overhead product stream into a gas-permeation membrane apparatus;
    (e) withdrawing from said membrane apparatus a sales- or fuel-grade gas methane product stream;
    (f) withdrawing from said membrane apparatus a carbon-dioxide-enriched gas permeate stream;
    (g) compressing the carbon-dioxide-enriched gas permeate stream;
    (h) recycling the compressed permeate stream for use in the process;
    (i) introducing the liquid carbon-dioxide-enriched bottom product stream as a feed stream into a low-temperature purification distillation column;
    (j) withdrawing a purified carbon dioxide overhead product stream from said purification column; and
    (k) withdrawing a bottom product stream containing essentially all of the undesirable impurities.

22. The process of claim 21 wherein the recycled, compressed permeate stream is introduced directly into the said distillation column.

23. A process for the separation of a landfill feed gas stream, having a high concentration of methane and carbon dioxide and containing undesirable trace gas impurities, into an enriched methane product stream and a carbon dioxide product stream, which process comprises:
    (a) introducing a dried, compressed, landfill feed gas stream into a cryogenic distillation column;
    (b) withdrawing a methane-enriched overhead product stream, essentially free of impurities, from said distillation column;
    (c) withdrawing an enriched liquid carbon dioxide bottom product stream, containing essentially all of the undesirable impurities, from said distillation column;
    (d) introducing the carbon dioxide bottom product stream as a feed stream into a low-temperature purification distillation column;
    (e) withdrawing a purified carbon dioxide overhead product stream from said purification distillation column; and
    (f) withdrawing a bottom product stream containing essentially all of the undesirable impurities from said purification distillation column.

24. The process of claim 23 wherein the feed gas stream has a concentration of both carbon dioxide and methane of over about 90 mole percent, and the carbon dioxide and methane are present in generally about equal concentrations.

25. The process of claim 23 wherein the feed gas stream comprises from about 30 to 70 mole percent of carbon dioxide and 30 to 70 mole percent of methane.

26. The process of claim 23 wherein the methane-enriched overhead product stream from said distillation comprises about 10 to 40 mole percent of carbon dioxide.

27. The process of claim 23 wherein the undesirable impurities comprise sulfur compounds, halogenated hydrocarbon compounds, ketones and hydrocarbons.

28. The process of claim 23 wherein the purification column is operated at a pressure below 200 psi and at less than −40° F.

29. The process of claim 28 wherein the temperature gradient in the purification column is less than 5° F.

30. A process for the separation of a landfill feed gas stream having a high concentration of both methane and carbonn dioxide and containing undesirable trace gas impurities comprising sulfur compounds, halogenated hydrocarbon compounds, ketones and hydrocarbons, which process comprises:
    (a) introducing a dried, compressed, landfill feed gas stream into a cryogenic distillation column;
    (b) withdrawing from said distillation column a methane-enriched overhead product stream essentially free of the trace gas impurities; and (c) withdrawing from said distillation column a liquid carbon-dioxide-enriched bottom product stream containing essentially all of the undesirable trace gas impurities.

31. The process of claim 30 wherein the feed gas stream has a concentration of both carbon dioxide and methane of over about 90 mole percent, and the carbon dioxide and methane are present in generally about equal concentrations.

* * * * *